(12) United States Patent
Yuan et al.

(10) Patent No.: US 8,513,408 B2
(45) Date of Patent: Aug. 20, 2013

(54) CALCIUM STABLE HIGH ACYL GELLAN GUM FOR ENHANCED COLLOIDAL STABILITY IN BEVERAGES

(75) Inventors: C. Ronnie Yuan, San Diego, CA (US); Neil Morrison, San Diego, CA (US); Ross Clark, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 1934 days.

(21) Appl. No.: 11/136,026

(22) Filed: May 24, 2005

(65) Prior Publication Data

US 2005/0266138 A1 Dec. 1, 2005

Related U.S. Application Data

(60) Provisional application No. 60/574,215, filed on May 26, 2004.

(51) Int. Cl.
*C08B 37/00* (2006.01)
(52) U.S. Cl.
USPC ............. 536/114; 426/573; 435/41; 435/101; 435/170; 536/123.1; 536/123.12; 516/105; 516/107
(58) Field of Classification Search
USPC ............................................ 435/41; 426/573
See application file for complete search history.

(56) References Cited

U.S. PATENT DOCUMENTS

| | | | |
|---|---|---|---|
| 4,326,052 A | 4/1982 | Kang et al. | |
| 4,326,053 A | 4/1982 | Kang et al. | |
| 4,377,636 A | 3/1983 | Kang et al. | |
| 4,385,123 A | 5/1983 | Kang et al. | |
| 4,385,125 A | 5/1983 | Preti et al. | |
| 5,112,445 A * | 5/1992 | Winston et al. | 162/178 |
| 5,190,778 A | 3/1993 | Clare et al. | |
| 5,534,286 A * | 7/1996 | Chalupa et al. | 426/573 |
| 5,597,604 A | 1/1997 | Chalupa et al. | |
| 5,641,532 A | 6/1997 | Pflaumer et al. | |
| 5,654,027 A | 8/1997 | Chalupa | |
| 6,242,035 B1 * | 6/2001 | Clark et al. | 426/573 |
| 7,147,885 B2 | 12/2006 | Asano et al. | |
| 7,887,866 B2 | 2/2011 | Bower et al. | |
| 2002/0146499 A1 * | 10/2002 | Valli et al. | 426/580 |
| 2003/0077371 A1 | 4/2003 | Asano et al. | |

FOREIGN PATENT DOCUMENTS

| | | |
|---|---|---|
| EP | 0012552 | 1/1982 |
| EP | 470870 A1 * | 2/1992 |
| JP | 10-234316 | 9/1998 |
| JP | 2000-333620 | 12/2000 |
| JP | 2001-178411 | 7/2001 |
| JP | 2001-316274 | 11/2001 |
| WO | WO 9964468 A1 * | 12/1999 |
| WO | 2000-41579 | 7/2000 |

OTHER PUBLICATIONS

Valli, R.C. et al. "Gellan Gum." in: Cho, S.S. et al., Handbook of Dietary Fiber (New York, Marcel Dekker, Inc., 2001), Chapter 35, 26 pages.*
Giavasis, I et al. Gellan gum. Critical Reviews in Biotechnology. 2000. 20(3): 177-211.*
Igoe, Hui, Dictionary of Food Ingredients (4th ed) 2001 Springer-Verlag, pp. 64-65.
Edited by Phillips & Williams, CRC Press Woodhead Publishing, Handbook of Hydro Colloids, 2nd ed. 2009, pp. 204-206.
Kang et al., "Agar-like Polysaccharide Produced by a *Pseudomonas* Species: Production and Basic Properties," Applied and Environmental Microbiology, May 1982, p. 1086-1091, vol. 43, No. 5, American Society of Microbiology, Washington DC.
Japanese Office Action for Japanese Application No. 2007-515227, dated Feb. 14, 2013, consisting of 4 pages.

* cited by examiner

*Primary Examiner* — Allison Ford
*Assistant Examiner* — Susan E Fernandez
(74) *Attorney, Agent, or Firm* — Sutherland Asbill & Brennan LLP

(57) ABSTRACT

A low calcium sensitive (calcium stable) high acyl gellan gum is prepared for enhanced colloidal stability in beverages. The low calcium sensitive high acyl gellan gum has superior suspension performance for colloidal stability compared to other high acyl gellan gums. The low calcium sensitive high acyl gellan gum is prepared by adjusting the pH of a gellan fermentation broth (polymer solution) prior to pasteurization and reducing the pasteurization hold time compared to conventional pH levels and hold times.

16 Claims, 1 Drawing Sheet

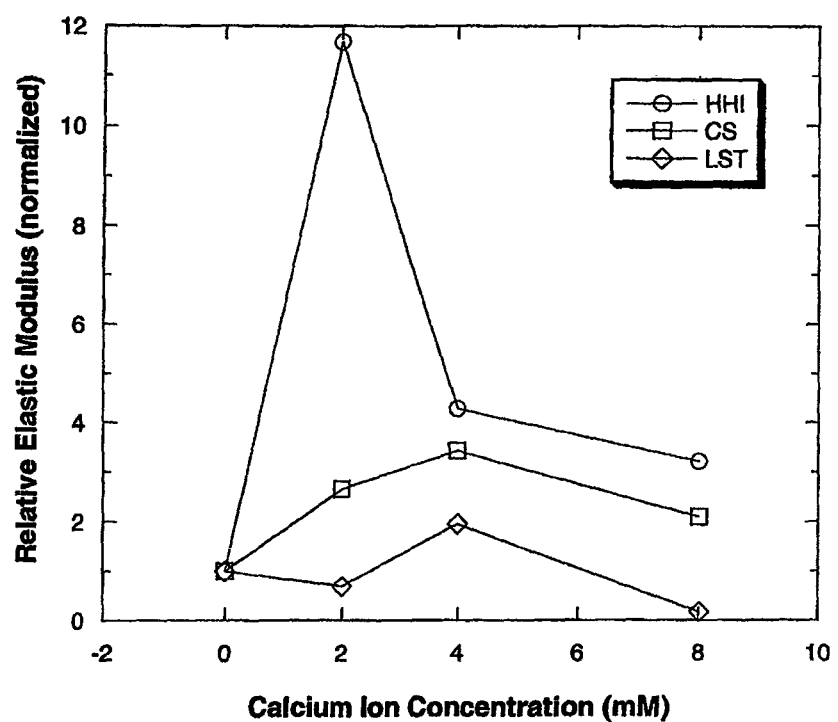

CALCIUM STABLE HIGH ACYL GELLAN GUM FOR ENHANCED COLLOIDAL STABILITY IN BEVERAGES

CROSS-REFERENCE TO RELATED APPLICATIONS

This application claims the benefit of U.S. Provisional Patent Application No. 60/574,215, filed May 26, 2004, entitled "Low Calcium Sensitive High Acyl Gellan Gum For Enhanced Colloidal Stability In Beverages"

FIELD OF THE INVENTION

This invention relates to calcium stable (low calcium sensitive) high acyl gellan gum and processes to prepare calcium stable high acyl gellan gum. The invention also relates the use of a family of calcium stable high acyl native gellan gums for enhanced colloidal stability and particle suspensions in beverage.

BACKGROUND OF THE INVENTION

Gums, also called hydrocolloids, are polysaccharides. Polysaccharides are polymers of simple sugar building blocks which have been in use since about 1900. Use of gums has increased throughout the century particularly in the past 40 years and today they are used in a wide variety of products and processes. Certain micro-organisms are capable of producing polysaccharides with properties differing from those of gums from more traditional sources. The best example of such microbially-produced polysaccharides is xanthan gum. More recently discovered examples are welan gum, rhamsan gum and gellan gum.

Gellan gum, first discovered in 1978, is produced by strains of the species *Sphingomonas elodea* [formerly *Pseudomonas elodea*], in particular strain ATCC 31461 [Kang, K. S. et al EP 12552 and U.S. Pat. Nos. 4,326,052; 4,326,053; 4,377,636 and 4,385,125]. Commercially this gum is produced as an extracellular product by aqueous cultivation of the micro-organisms in a medium containing appropriate carbon, organic and inorganic nitrogen and phosphate sources and suitable trace elements. The fermentation is carried out under sterile conditions with strict control of aeration, agitation, temperature and pH [Kang et al, Appl. Environ. Microbiol., 43, [1982], 1086]. When fermentation is complete, the produced viscous broth is pasteurized to kill viable cells prior to recovery of the gum. The gum can be recovered in several ways. Direct recovery from the broth yields the gum in its native or high acyl [HA] form. Recovery after deacylation by treatment with a base yields the gum in its low acyl [LA] form. Acyl groups present in the gum are found to influence its characteristics significantly.

The constituent sugars of gellan gum are glucose, glucuronic acid and rhamnose in the molar ratio of 2:1:1. These are linked together to give a primary structure comprising a linear tetrasaccharide repeat unit [O'Neill M. A., et al, Carbohydrate Res., 124, [1983], 123 and Jansson, P. E., et al., Carbohydrate Res., 124, [1983], 135]. In the native or high acyl [HA] form two acyl substituents, acetate and glycerate, are present. Both substituents are located on the same glucose residue and, on average, there is one glycerate per repeat unit and one acetate per every two repeat units. In the low acyl [LA] form, the acyl groups have been removed to produce a linear repeat unit substantially lacking such groups. Light scattering and intrinsic viscosity measurements indicate a molecular mass of approximately $5 \times 10^5$ daltons for [LA] gum [Grasdalen, H. et al., Carbohydrate Polymers, 7, [1987], 371]. X-ray diffraction analysis shows that gellan gum exists as a three-fold, left-handed, parallel double helix [Chandreskaran et al., Carbohydrate Res., 175, [1988], 1 181, [1988]23].

Low acyl [LA] gellan gums form gels when cooled in the presence of gel-promoting cations, preferably divalent cations, such as calcium and magnesium. The gels formed are firm and brittle. High acyl [HA] gellan gums do not require the presence of cations for gel formation and the gels formed have structural and rheological characteristics which are significantly affected by the acyl substituents. Thus the properties of [HA] gellan gels differ significantly from those of [LA] gellan gels. [HA] gels are typically soft and flexible and lack thermal hysteresis.

Typical gelation temperatures for [LA] gellan gums are in the range 30° C. to 50° C., depending upon the nature and concentration of the cations present. For purposes of this patent, gelation, set and melt temperatures are defined by measurement of the elastic modulus (G') value of the gel in an appropriate rheometer. Conditions used are a frequency of 10 radians/second with a strain level of 1-5%. In most cases, the appropriate temperature is judged by the rate of change in the modulus value. A rapid increase with cooling is the setting temperature; a sharp drop indicates the melt temperature when heating. Frequently, the temperature where the modulus goes above or below a value of 1 Pa is used as an index. Typical gelation temperatures for [HA] gellan gums are in the region of 70° C. The high gelation temperature of [HA] gellan gum can be advantageous in some applications such as fruit fillings where it can prevent flotation of the fruit. In other applications, however, such as ready-to-eat jellies and confectionery, the high gelation temperature can be a problem with regard to pre-gelation prior to depositing.

A wide range of gel textures can be produced through manipulation of blends of [HA] and [LA] gellan gum. However, it has been demonstrated that mixtures of [HA] and [LA] forms exhibit two separate conformational transitions at temperatures coincident with the individual components [Morris, E. R., et al., Carbohydrate Polymers, 30, [1996], 165-175]. No evidence for the formation of double helices having both [HA] and [LA] molecules has been found. This means that problems associated with the high gelation temperature of [HA] gellan gum still exist in blended systems.

It has been demonstrated that treatment conditions using strong bases such as potassium hydroxide during recovery influence both the composition and Theological properties of gellan gum [Baird, J. K., Talashek, T. A., and Chang, H., Proc. 6th International Conference on Gums and Stabilisers for the Food Industry, Wrexham, Clwyd, Wales. July 1991—Edited Phillips G. O., et al, published by IRL Press at OUP [1992], 479-487]. This suggests that control of acyl content by strong base treatment during the gum recovery process can lead to a diversity of textures. To date, however, this observation has not led to such control being realized on a commercial scale. Consequently, gellan gum remains available essentially in two forms only, i.e. [HA] and [LA].

Gellan gums have a wide variety of applications in food and non-food manufacture and the provision of a range of forms in addition to the basic [HA] and [LA] forms, i.e. a range of intermediate forms, other than blends, is desirable. Such new forms of gellan gums are potentially useful in the current search for suitable alternatives to gelatin.

The texture of native gellan gum is ideal for a number of commercial food applications, including milk-based products such as puddings, coffee creamers, drinks and desserts. The rheology of gellan gum at low dosage enables it to suspend fine particles such as cocoa in milk systems. As a result of these textural characteristics, gellan gum has long been sought for use in cultured dairy products, retorted dairy products and frozen dairy products.

U.S. Pat. No. 6,602,996, incorporated herein in its entirety, describes the production of high acyl gellan gum compositions which comprises a structure having linear tetrasaccharide repeat units of glucose residues to some of which residues are attached acetate and/or glycerate substituent groups wherein the ratio of acetate substituent groups to glycerate substituent groups is at least 1.

High acyl gellan gums have been used in yogurt drink products, for fruit pulp suspension, and in retort milk beverages but with limited success. The HA gellan samples used in retort milk beverages were not tested for setting temperature or thermal hysteresis tests, only for gel strength. The polymer failed to suspend colloids reproducibly because of this in appropriate gel strength test. Moreover, such high acyl gellan gum could not be used in neutral milk beverages due to off flavor issues with p-cresol development in UHT and HTST applications. The high acyl gellan gum had poor suspension capability for cocoa in dairy or soy based systems, or fruit pulp in juice beverages, due to partial deacylation or lower set temperatures and measurable thermal hysteresis. Such high acyl gellan gum compositions are not calcium stable and tend to break down. Unless produced under appropriate conditions, the HA gellan gum contains some LA components which damage its functional properties in these systems.

Kelcogel, low acyl gellan, a commercially available product in the USA since 1993 behaves quite differently in beverages, it requires sequestrant prior to hydration, is protein and calcium sensitive and has a much narrower working range for varying calcium levels than these new high acyl gellan molecules

BRIEF SUMMARY OF THE INVENTION

The present invention is directed to a calcium stable (low calcium sensitive) high acyl gellan gum for enhanced colloidal stability in beverages. The calcium stable high acyl gellan gum has superior suspension performance for colloidal stability compared to other high acyl gellan gums.

In accordance with an embodiment of the invention, the calcium stable high acyl gellan gum is prepared by adjusting the pH of a gellan fermentation broth (polymer solution) prior to pasteurization and reducing the pasteurization hold time compared to and conventional pH levels and hold times.

In a particular embodiment, the average pH of the gellan fermentation broth is maintained below about 7.5, preferably below about 6.8, and more preferably below about 6.5, throughout the process of producing the calcium stable gellan and particularly during pasteurization or a heat treatment step. The hold time is typically less than about 2 minutes, preferable about 0.5 to about 1.5 minutes.

The resulting gellan gum has a high set point, greater than 75-80° C., with thermoreversible behavior and low calcium sensitivity pasteurization.

In accordance with another embodiment, beverages are prepared with the calcium stable high acyl gellan gum. Such beverages include milk-based or other dairy-based beverages, soy-based beverages, fruit-based beverages, and various nutrition-based or meal replacement beverages. The calcium stable high acyl gellan gum provides good colloidal stability and particle suspension, and has low sensitivity to calcium that is found in, or added to, the beverages.

BRIEF DESCRIPTION OF THE DRAWINGS

FIG. 1 shows the effect of calcium ion concentration on the relative elastic modulus of the three 0.035% gellan gum solutions.

DETAILED DESCRIPTION OF THE INVENTION

This present invention is directed to the preparation and use of calcium stable high acyl native gellan gums for enhanced colloidal stability and particle suspensions in beverages.

In the native form of gellan, the polysaccharide is modified by acetyl and glycerate substituents on the same glucose residue.

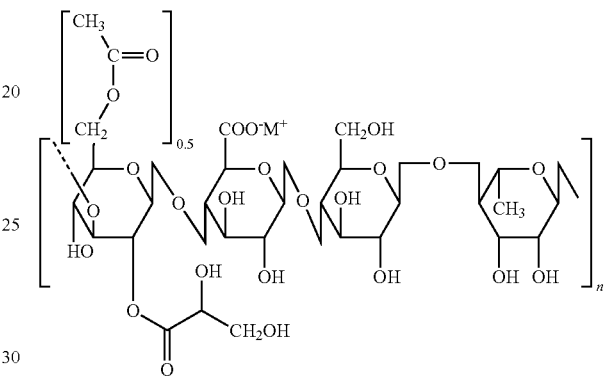

These residues produce a high acyl gellan gum molecule that displays excellent colloidal suspension capability. It is critical that any deacylation of these substituents is minimized to maximize the functionality of the high acyl gellan gum.

On average there is one glycerate per tetrasaccharide repeat unit and one acetate per every two tetrasaccharide repeat units. Direct recovery of the native broth yields gellan in its native or high acyl form, which is modified by P. Elodea with acetyl and glyceryl substituents on one glucose sugar on the polymer backbone. Isolation of high acyl gellan in this native form yields a soft flexible gel and the polymer undergoes a thermo-reversible sol-gel transition at high temperature (>75° C.).

Native gellan can be partially deacylated during fermentation, post-fermentation treatments, or recovery by alkali, enzymes or high temperature. Depending on the mode of action, partial deacylation of gellan could lead to undesirable properties such as low gelation temperature (30-70° C.), brittle textures and a thermally irreversible gel network, and/or thermal hysteresis. Moreover, a product with a lower set temperature (less than 70° C.) but displaying low thermal hysteresis has a reduced ability to stabilize colloids. Removal of acyl groups makes the gellan more reactive to calcium which limits the application in products such as milk-based beverages and also increases the gellan molecules affinity for milk proteins and fruit proteins, leading to poor long term stability of colloidal suspensions.

The present invention is directed to the discovery that minimizing deacylation and producing low thermal hysteresis produces a calcium stable high acyl gellan. Such gellan has enhanced colloidal stability in beverages allowing for greatly enhanced suspension performance. The gellan has a high set point (greater than 75-80° C.) with thermo-reversible behavior and low calcium sensitivity.

The calcium stable high acyl gellan gums are produced under controlled conditions that minimize either random or blocky deacylation of gellan molecules. These native gellan molecules have high gelation temperature and minimal thermal hysteresis (setting the polymer and re-melting it) as characterized by a thermo-rheological test using an appropriate rheometer. Pasteurization or other forms of heat treatments above pH 7.5, in contrast, causes block or random deacylation.

The molecules of the calcium stable high acyl gellan gums also have low protein reactivity and calcium sensitivity compared to lower acyl type gellans with lower setting temperatures.

Stabilizing materials requires forming a network of polymers or proteins with a small size. If the pores in the network are too large, small colloidal materials can flow within the network. Some gel forming polymers can have large pore sizes. The calcium stable high acyl gellan gum of the invention has a small pore size as evidenced by its ability to stabilize even small colloidal material.

Stabilizing materials requires forming a network of polymers or proteins with a small size. If the pores in the network are too large, small colloidal materials can flow within the network. Some gel forming polymers can have large pore sizes. The calcium stable high acyl gellan gum of the invention has a small pore size as evidenced by its ability to stabilize even small colloidal material.

The unique properties of the calcium stable high acyl gellan gums enable the molecules to form stable fluid gels easily under various processing conditions. For example, at very low concentrations (0.01 to 0.05%), the calcium stable high acyl gellan gums can be used in a wide variety of beverages to stabilize suspensions of particulate matters such as fruit pulps, cocoa powders, minerals, gel bits, soy protein, whey microparticles, emulsified flavor oils and other protein aggregates without imparting high apparent viscosity. At higher use levels (0.06 to 0.20%), the calcium stable high acyl gellan gums can provide a rich and viscous mouthfeel in addition to stabilizing particle suspensions.

Colloidal or particle suspensions stabilized by the calcium stable high acyl gellan gums have a very uniform appearance and show excellent long-term stability. Moreover, insoluble or soluble calcium salts can be added to fortify beverages without destabilizing the weak gel network unlike the more calcium sensitive low acyl gellan types where the beverage product initially thickens then destabilizes over time causing the suspended particles to settle.

The calcium stable high acyl gellan gum is prepared by adjusting the pH of a gellan fermentation broth prior to pasteurization. The average pH of the polymer solution or fermentation broth is maintained below about 7.5, preferably below about 6.8, and more preferably below about 6.5, throughout process and particularly during pasteurization or a heat treatment step. Heating at a pH higher than 7.5 must be avoided.

The pH of the broth is adjusted by adding a suitable acid such as sulfuric acid, hydrochloric acid, phosphoric acid, or citric acid, until the desired pH is reached.

The broth is pasteurized at 80° C. to about 110° C., preferably about 95° C. for less than about 5 minutes, preferable about 0.5 to about 1.5 minutes, typically about 1 minute.

The gellan is then precipitated such as by the addition of an alcohol, such as isopropyl alcohol, or ethanol.

The precipitated gellan fibers are dried at a suitable temperature, for example about 40° C. to about 100° C., typically about 75° C., until a solids content of about 85% to about 98% is reached, preferably about 92 to about 95% solids. The dried fiber is then milled into fine powders-by any suitable method.

The calcium-stable high acyl gellan can be added to any suitable beverage that contains suspended particles. Such beverages include, but are not limited, to chocolate milk and other milk-based or dairy-based beverages, soy-based beverages, fruit-based beverages, various nutrition-based or meal replacement beverages, and fiber-rich laxative drinks.

Example 1

Process for Making Calcium Stable (CS) HA Gellan Gum and Comparative Gums

A calcium stable (CS) HA gellan with a high gel set temperature and low thermal hysteresis, a high hysteresis index (HHI) gellan, and a low set temperature (LST) gellan were prepared. Three liters of warm native gellan broth (50° C., pH 6.5) were divided into three 1-liter portions. Each 1-liter broth was processed differently to produce the three HA gellan samples.

The CS HA gellan was prepared by adjusting the pH of the broth to pH 5.5 with dilute sulfuric acid. The broth was then pasteurized at 95° C. for 1 minute, followed by precipitation with 3 liters of 85% isopropyl alcohol in a blender.

The HHI HA gellan was prepared by adding 1.8 g of 45% (w/w) KOH to the broth and agitating at 50° C. for 1 hr. The pH of the broth was adjusted to pH 5.5 with dilute sulfuric acid prior to pasteurization and precipitation as described above.

The LST HA gellan was prepared by adjusting the pH of the broth to 7.5 with dilute KOH (5%, w/w) solution. The broth was then pasteurized at 95° C. for 5 min, followed by precipitation with 3 liters of 85% isopropyl alcohol in a blender.

The precipitated gellan fibers were dried at 75° C. to 92 to 95% solids and then milled into fine powders.

Example 2

Differentiation of the Three Forms of HA Gellan Gum

Thermal rheological properties of the HA gellan gums were tested using a rheometer. 1.5 grams of each gellan gum powder was hydrated in 294 g of DI water by heating to 95° C. under constant agitation. Six ml of 0.3 M calcium chloride solution was added to the hot solution. Hot DI water was added to adjust the final weight of the solution to 300 g.

Rheological properties as a function of temperature of the hot solution were measured using a Bohlin CVO rheometer with a 4-cm 4° cone and plate system operated under a oscillatory mode at 0.2 strain and 1 hertz from 95° C. to 20° C. (4° C./min), followed immediately by reheating from 20° C. to 95° C. (4° C./min). Two thermal rheological properties, gel set temperature and hysteresis index, were defined and used to differentiate HA gellan gums. Gel set temperature was defined as the temperature at which the elastic modulus (G') of the sample reaches 1 Pa during cooling. Hysteresis index was defined as the ratio of G' at gel set temperature during reheating to G' at gel set temperature during cooling. Thermal rheological properties of the three HA gellan samples were measured and compared using this protocol.

The thermal rheological properties of the three samples are shown in Table 1. The CS gellan had the highest gelling temperature and the lowest hysteresis index among the three HA samples. The HHI sample had the highest hysteresis index whereas the LST sample had the lowest gel set temperature.

TABLE 1

Comparison of thermal rheological properties of three HA gellan gums

| | Cs (Inv.) | HHI | LST |
|---|---|---|---|
| Gel Set Temperature (° C.) | 85.7 | 83.6 | 68.6 |
| Hysteresis Index | 7 | 102 | 14 |

Example 3

Effect of Calcium on HA Gellan Gums

The effect of calcium ions on the elastic modulus of the three HA gellan samples were observed. A 0.035% gellan solution was prepared in DI water by heating to 90° C. Desired amounts of calcium ions (0, 2, 4, and 8 mM) were added to the hot solution before the solution was cooled in an ice bath to 12° C. under constant agitation. After resting at room temperature for 18 hours, the elastic modulus was measured at 0.2 strain and 1 hertz using a Vilastic V-E System rheometer.

The effect of calcium ion concentration on the relative elastic modulus of the three 0.035% gellan gum solutions is shown in FIG. 1. The relative elastic modulus values were normalized in relation to the elastic modulus at 0 concentration of calcium.

Elastic modulus of a solution is a good indicator of the solution's structural attributes and its ability to suspend particulate matters. A certain level of elastic modulus is required to keep particles suspended in the solution, but too high of an elastic modulus could mean a very structured network with undesirable sensory attributes for a beverage product.

As shown in FIG. 1, the elastic modulus of the HHI gellan solution was extremely sensitive to calcium ion concentration, showing sharp rise and fall with increasing calcium concentration. For the LST sample, the solution lost most of its modulus in the presence of 8 mM calcium, suggesting poor particle suspension properties at higher calcium levels. In comparison, the CS sample showed a more stable elastic modulus curve with increasing calcium concentration.

Example 4

Sensitivity of Hydration to Calcium

Low acyl (LA) gellan hydrates poorly in the presence of calcium ions. On the other hand, CS HA gellan hydrates in the presence of calcium ions.

Gellan solutions (0.035%) containing 2 mM of calcium ions were prepared from the CS HA gellan and a LA gellan gum using a similar protocol described in Example 3. Two solutions from each gellan sample were prepared. For the first solution, the calcium was added after heating to 90° C. For the second solution, the gum was added directly to 2 mM calcium solution before it is heated to 90° C. The elastic modulus data of these solutions are shown in Table 2.

TABLE 2

Elastic modulus (dyne/cm$^2$) of gellan solutions as affected by hydration conditions

| Hydration Condition | CS HA Gellan | LA Gellan |
|---|---|---|
| Calcium added after heating | 2.25 | 1.89 |
| Calcium added before heating | 2.81 | 0.05 (gellan not hydrated) |

It is clear from the elastic modulus data that the CS HA gellan can hydrate and develop a gellan network in the presence of calcium. In contrast, the LA gellan does not hydrate at all if the calcium is added before heating.

Example 5

Cocoa Suspension in Chocolate Beverage With HA Gellan

CS HA gellan can suspend cocoa particles in a chocolate beverage in contrast to HHI and LST HA gellan gums.

Chocolate beverages stabilized with HA gellan gums were made using the recipe shown in Table 3.

TABLE 3

Chocolate beverage formulation

| INGREDIENTS | PERCENTAGE |
|---|---|
| Water | 85.97 |
| Sugar | 8.00 |
| Non-Fat Dry Milk Powder | 5.00 |
| Cocoa Powder | 1.00 |
| HA gellan gum | 0.03 |

Procedure
1. Mix together all dry ingredients.
2. Add premixed dry ingredients to water under agitation.
3. Heat the solution to 87° C.
4. Homogenize at 1500 psi first stage, 500 psi second stage.
5. UHT process 6 sec at 138° C.
6. Fill under aseptic conditions at 25° C.

The suspension of cocoa powder and the appearance of the beverage samples were assessed visually by three panelists. The results shown in Table 4 indicate that the CS HA gellan performed much better than either HHI or LST gellan.

TABLE 4

Cocoa suspension performance of HA gellan gums in chocolate beverage

| | CS | HHI | LST |
|---|---|---|---|
| Cocoa suspension | Yes | Yes | No |
| Beverage appearance | Smooth | Phase separation, very structured appearance | Smooth, with thick layer of cocoa at bottom |

Example 6

Cocoa Suspension and Mineral Stabilization in Calcium Fortified Soy Chocolate Milk CS HA gellan has the ability to suspend cocoa particles and calcium minerals in soy chocolate milk.

Calcium fortified soy chocolate milk stabilized with CS HA gellan gums were prepared using the recipe shown in Table 5.

TABLE 5

Chocolate beverage formulation

| INGREDIENTS | PERCENTAGE |
|---|---|
| Water | 86.67 |
| Sugar | 8.00 |
| Soy protein isolate | 4.00 |
| Cocoa Powder | 1.00 |
| Tricalcium Phosphate | 0.3 |
| HA gellan gum | 0.03 |

Procedure
1. Mix together all dry ingredients.
2. Add premixed dry ingredients to water under agitation.
3. Heat the solution to 87° C.
4. Homogenize at 1500 psi first stage, 500 psi second stage.
5. UHT process 6 sec at 138° C.
6. Fill under aseptic conditions at 25° C.

Visual evaluation of the soy chocolate milk stabilized with CS HA showed no signs of cocoa particle or calcium mineral sedimentation.

While the invention has been described with respect to specific examples including presently preferred modes of carrying out the invention, those skilled in the art will appreciate that there are numerous variations and permutations of the above described systems and techniques that fall within the spirit and scope of the invention.

The invention claimed is:

1. A process for preparing a calcium stable high acyl gellan gum, comprising:
    pasteurizing a gellan gum fermentation broth consisting essentially of a native gellan gum and an acid to produce the high acyl gellan gum, wherein the fermentation broth is maintained at a pH from 5.5 to 6.5 during the pasteurizing;
    wherein the acid is selected from the group consisting of sulfuric acid, hydrochloric acid, phosphoric acid, citric acid, and combinations thereof; and
    wherein the high acyl gellan gum has a set temperature of greater than 70° C.

2. The process of claim 1 wherein the gellan gum fermentation broth is pasteurized at a temperature between about 80° C. and about 110° C.

3. The process of claim 1 wherein the pasteurization hold time is less than about 2 minutes.

4. The process of claim 1 wherein the pasteurization hold time is about 0.5 to about 1.5 minutes.

5. The process of claim 1 further comprising, after pasteurizing, precipitating the high acyl gellan gum from the gellan gum fermentation broth.

6. The process of claim 1 wherein the high acyl gellan gum has a set temperature of greater than 75° C.

7. The process of claim 1 wherein the high acyl gellan gum has a set temperature of greater than 80° C.

8. A process of preventing deacylation of acetyl and glycerate substituents during preparation of gellan gum comprising:
    pasteurizing a gellan gum fermentation broth consisting essentially of a native gellan gum and an acid to produce the gellan gum, wherein the fermentation broth is maintained at a pH below about 6.8 during the pasteurizing;
    wherein the acid is selected from the group consisting of sulfuric acid, hydrochloric acid, phosphoric acid, citric acid, and combinations thereof; and
    wherein the gellan gum has a set temperature of greater than 70° C.

9. The process of claim 8 wherein the pH of the gellan gum fermentation broth is below about 6.5.

10. The process of claim 8 wherein the gellan gum fermentation broth is pasteurized at a temperature between about 80° C. and about 110° C.

11. The process of claim 8 wherein the pasteurization hold time is less than about 2 minutes.

12. The process of claim 11 wherein the pasteurization hold time is about 0.5 to about 1.5 minutes.

13. The process of claim 8 wherein the pH of the gellan gum fermentation broth is below about 5.5.

14. A gellan gum having a set point greater than 70° C. prepared by pasteurizing a gellan gum fermentation broth consisting essentially of a native gellan gum and an acid, wherein the fermentation broth is maintained at a pH from 5.5 to 6.5 during the pasteurizing; and
    wherein the acid is selected from the group consisting of sulfuric acid, hydrochloric acid, phosphoric acid, citric acid, and combinations thereof.

15. The gellan gum of claim 14 wherein the pasteurization hold time is less than about 2 minutes.

16. The gellan gum of claim 14 wherein the pasteurization hold time is about 0.5 to about 1.5 minutes.

* * * * *